(12) United States Patent
Simmelink et al.

(10) Patent No.: US 8,999,866 B2
(45) Date of Patent: Apr. 7, 2015

(54) BALLISTIC-RESISTANT ASSEMBLIES WITH MONOLAYERS OF HIGH-PERFORMANCE POLYETHYLENE MULTIFILAMENT YARNS

(71) Applicants: Joseph Arnold Paul Maria Simmelink, Sittard (NL); Jacobus Johannes Mencke, Maastricht (NL); Martinus Johannes Nicolaas Jacobs, Heerlen (NL); Roeloef Marissen, Born (NL)

(72) Inventors: Joseph Arnold Paul Maria Simmelink, Sittard (NL); Jacobus Johannes Mencke, Maastricht (NL); Martinus Johannes Nicolaas Jacobs, Heerlen (NL); Roeloef Marissen, Born (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 14/012,413

(22) Filed: Aug. 28, 2013

(65) Prior Publication Data

US 2014/0060307 A1   Mar. 6, 2014

Related U.S. Application Data

(62) Division of application No. 12/576,239, filed on Oct. 8, 2009, now abandoned, which is a division of application No. 10/584,285, filed as application No. PCT/NL2004/000903 on Dec. 23, 2004, now Pat. No. 7,618,706.

(30) Foreign Application Priority Data

Jan. 1, 2004   (WO) ............... PCT/NL04/00029

(51) Int. Cl.
*D01D 5/18*    (2006.01)
*A61L 17/04*   (2006.01)
(Continued)

(52) U.S. Cl.
CPC . *D01D 5/18* (2013.01); *A61L 17/04* (2013.01); *A61L 27/16* (2013.01); *D01D 4/02* (2013.01);
(Continued)

(58) Field of Classification Search
CPC ........ A41D 1/04; A41D 27/12; F41H 5/0478; B32B 5/26; B32B 5/12; B32B 5/02; B32B 27/02; B32B 38/00; B32B 27/04
USPC ............... 2/2.5; 89/36.01; 428/105, 107, 108, 428/109, 113, 364, 365, 911; 442/134, 135
See application file for complete search history.

(56) References Cited

U.S. PATENT DOCUMENTS

| | | | |
|---|---|---|---|
| 4,054,468 | A | 10/1977 | Honnaker et al. |
| 4,413,110 | A | 11/1983 | Kavesh et al. |

(Continued)

FOREIGN PATENT DOCUMENTS

| | | |
|---|---|---|
| CN | 1432077 | 7/2003 |
| EP | 0 064 167 A | 11/1982 |

(Continued)

OTHER PUBLICATIONS

Kilburn & Strode, Opponent's Letter to EPO dated Sep. 19, 2014, pp. 1-12.

(Continued)

*Primary Examiner* — Arti Singh-Pandey
(74) *Attorney, Agent, or Firm* — Nixon & Vanderhye P.C.

(57) ABSTRACT

Ballistic-resistant assemblies include monolayers formed of high-performance polyethylene multi-filament yarns. The assemblies have an areal density of at least 1.5 kg/m² and a specific energy absorption of at least 300 J·m²/kg as measured against a 9*19 mm FMJ Parabellum bullet according to a test procedure based on Stanag 2920.

3 Claims, 3 Drawing Sheets

(51) Int. Cl.
*A61L 27/16* (2006.01)
*D01D 4/02* (2006.01)
*D01F 6/04* (2006.01)
*D02G 3/02* (2006.01)
*F41H 5/04* (2006.01)
*C08L 23/06* (2006.01)
*C08L 53/02* (2006.01)

(52) U.S. Cl.
CPC .. *D01F 6/04* (2013.01); *D02G 3/02* (2013.01); *F41H 5/0485* (2013.01); *F41H 5/0471* (2013.01); *C08L 23/06* (2013.01); *C08L 53/02* (2013.01); *C08L 2203/12* (2013.01); *D10B 2321/0211* (2013.01)

(56) References Cited

U.S. PATENT DOCUMENTS

| | | | |
|---|---|---|---|
| 4,473,617 A | | 9/1984 | Van Leeuwen et al. |
| 4,724,109 A | | 2/1988 | Yamashita et al. |
| 5,068,073 A | | 11/1991 | Pennings et al. |
| 5,248,471 A | | 9/1993 | Kavesh |
| 5,296,185 A | | 3/1994 | Chau et al. |
| 5,740,451 A | | 4/1998 | Muraki et al. |
| 6,000,055 A | * | 12/1999 | Citterio ............... 2/2.5 |
| 6,183,834 B1 | * | 2/2001 | van der Loo ............ 428/107 |
| 6,733,267 B2 | | 5/2004 | Chapman et al. |
| 6,746,975 B2 | * | 6/2004 | Kavesh ............... 442/135 |
| 6,916,533 B2 | | 7/2005 | Simmelink et al. |
| 7,618,706 B2 | | 11/2009 | Simmelink et al. |
| 2007/0145630 A1 | | 6/2007 | Simmelink et al. |

FOREIGN PATENT DOCUMENTS

| | | |
|---|---|---|
| EP | 0 110 021 A | 6/1984 |
| EP | 0 200 547 A | 11/1986 |
| EP | 0 213 208 | 3/1987 |
| EP | 0 472 114 | 2/1992 |
| JP | 58-5228 | 1/1983 |
| JP | 3-119105 | 5/1991 |
| JP | 5-106107 | 4/1993 |
| JP | 7-238416 | 9/1995 |
| JP | 2003-528994 | 9/2003 |
| WO | 94/12703 | 7/1994 |
| WO | 01/73173 | 10/2001 |
| WO | 01/73173 A | 10/2001 |
| WO | 2005/066401 | 7/2005 |

OTHER PUBLICATIONS

Spectra Shield® PCR, Spectra Performance Materials, AlliedSignal, Inc., VA (USA) 1996 (D8).
Spectra Shield® LCR, Spectra Performance Materials, AlliedSignal, Inc., VA (USA) 1996 (D9).
Spectra Shield® LCRw, Spectra Performance Fibers, Shield Product Specification, 2000 (D10).

* cited by examiner

BALLISTIC-RESISTANT ASSEMBLIES WITH MONOLAYERS OF HIGH-PERFORMANCE POLYETHYLENE MULTIFILAMENT YARNS

CROSS-REFERENCE TO RELATED APPLICATIONS

This application is a divisional of commonly owned U.S. application Ser. No. 12/576,239, filed Oct. 8, 2009 (now abandoned), which is a divisional of Ser. No. 10/584,285, filed Sep. 8, 2006 (now U.S. Pat. No. 7,618,706), which is the national phase application under 35 USC §371 of PCT/NL2004/000903, filed Dec. 23, 2004, and claims the benefit of priority of PCT/NL04/00029, filed Jan. 1, 2004, the entire contents of which are hereby incorporated by reference.

FIELD

The invention relates to a continuous process for making high-performance polyethylene (HPPE) multifilament yarn comprising the steps of
a) making a 3-25 mass % solution of ultra-high molar mass polyethylene having an intrinsic viscosity as measured on solutions in decalin at 135° C. of between about 8 and 40 dl/g, in a solvent;
b) spinning of the solution through a spinplate containing at least 5 spinholes into an air-gap to form fluid filaments, while applying a draw ratio $DR_{fluid}$;
c) cooling the fluid filaments to form solvent-containing gel filaments;
d) removing at least partly the solvent from the filaments; and
e) drawing the filaments in at least one step before, during and/or after said solvent removing, while applying a draw ratio $DR_{solid}$ of at least 4.

The invention further relates to a high-performance polyethylene multifilament yarn, and to semi-finished or end-use products containing said yarn, especially to various kinds of ropes and ballistic-resistant composites.

BACKGROUND AND SUMMARY

Such a process is known from WO 01/73173 A1. A polyethylene multifilament yarn with a tensile strength of 4.0 GPa for a yarn containing 60 filaments is described in this patent publication, which was made by a continuous process comprising the steps of
a) making a solution of 8 mass % of ultra-high molar mass polyethylene homopolymer having an intrinsic viscosity of 27 dl/g in mineral oil;
b) spinning of the solution through a spinplate containing 60 spinholes, each having a tapered inflow zone of unspecified dimension and a downstream zone of about 1 mm diameter and length/diameter ratio (L/D) of 40, into an air-gap of about 3.2 mm to form fluid filaments, while applying a draw ratio $DR_{fluid}$ of 15;
c) cooling the fluid filaments in a water quench bath to form solvent-containing gel filaments;
d) removing the solvent from the filaments by extraction with trichlorotrifluoroethane; and
e) drawing the filaments in five steps before, during and after removing the solvent applying a draw ratio $DR_{solid}$ of 36.5.

A high-performance polyethylene multifilament yarn is herein understood to mean a yarn containing at least 5 filaments made from ultra-high molar mass, or ultra-high molecular weight, polyethylene having an intrinsic viscosity (IV, as measured on solutions in decalin at 135° C.) of at least about 4 dl/g (UHPE), the yarn having a tensile strength of at least 3.0 GPa and a tensile modulus of at least 100 GPa (hereinafter also simply referred to as strength or modulus). Such HPPE yarns have a properties profile that make them an interesting material for use in various semi-finished and end-use products, like ropes and cords, mooring lines, fishing nets, sports equipment, medical applications, and ballistic-resistant composites.

Within the context of the present invention a yarn is understood to be an elongate body comprising multiple individual filaments having cross-sectional dimensions much smaller than their length. The filaments are understood to be continuous filaments; that is being of virtually indefinite length. The filaments may have cross-sections of various geometrical or irregular shapes. Filaments within a yarn may be parallel or entangled to one another; the yarn may be linear, twisted or otherwise departed from a linear configuration.

It is well known in the field of fibres and yarn technology that a multifilament yarn shows lower tenacity or tensile strength than the strength as measured on its constituent individual filaments. In general, the more filaments a yarn contains, the lower its tensile strength (breaking strength per unit of cross-sectional area, e.g. $N/m^2$ or Pa).

FIG. 1 confirms the said decrease in tensile strength with increasing number of filaments in a yarn for some commercially available HPPE yarns; by showing tensile strength (TS) data for the indicated Spectra® and Dyneema® grades, as collected from brochures and web-sites of the respective producers and plotted versus the logarithm of the number of filaments (n) in the yarn. It is thus concluded that the strength of a multifilament yarn is always lower than that of its individual filaments.

It is furthermore well known, that spinning of high-strength multifilament yarn becomes increasingly difficult the higher the number of filaments in the yarn as spun, one of the likely reasons being differences in spinning and drawing conditions, and subsequently in properties, occurring between filaments. For a polyethylene multifilament yarn spinning process to be commercially viable on industrial scale, it is important that such process can be run continuously without interruptions and with high throughput rate, with a high number of filaments in the as-spun yarn.

In many of the above-mentioned applications, critical properties of HPPE yarn determining performance in use include tensile properties and creep behaviour. There is thus a constant need in industry for HPPE multifilament yarn showing improved performance, like improved tensile properties. Although various studies suggest the theoretical strength of a UHPE filament to be in the range 10-20 GPa, the strongest yarns available show much lower strength; for example a 780-filament Dyneema® SK75 yarn has a strength of about 3.5 GPa. More specifically therefore, there is a need for a process that enables production of such higher tensile strength yarn on industrial scale.

According to the present invention, this is provided by a process
wherein in step b) each spinhole comprises a contraction zone with a gradual decrease in diameter from $D_0$ to $D_n$ with a cone angle in the range 8-75°, and wherein the spinhole comprises a zone downstream of the contraction zone of constant diameter $D_n$ with a length/diameter ratio $L_n/D_n$ of from 0 to at most 25, to result in a fluid draw ratio $DR_{fluid} = DR_{sp} * DR_{ag}$ of at least 150, wherein $DR_{sp}$ is the draw ratio in the spinholes and $DR_{ag}$ is the draw ratio in the air-gap, with $DR_{sp}$ being greater than 1 and $DR_{ag}$ at least 1.

With the process according to the invention a HPPE multifilament yarn can be obtained that has higher tensile strength than any known HPPE yarn containing at least 5 filaments, especially an as-spun yarn; more specifically a HPPE multifilament yarn containing n filaments has and having a tensile strength TS obeying the formula TS≥f*(n$^{-0.065}$) GPa, wherein factor f is at least 5.8 and n is at least 5.

DETAILED DESCRIPTION

Figure 1:
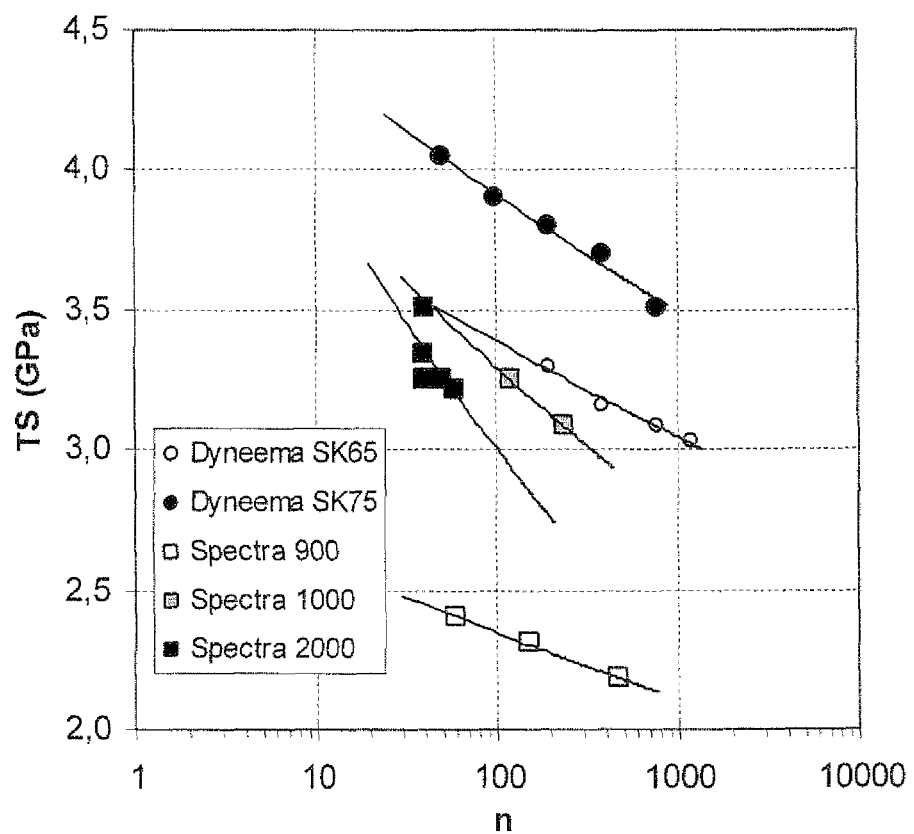
FIG. 1 is a plot of tensile strength (TS) versus the number of filaments (n) for some commercially available HPPE yarns, i.e., Spectra® brand and Dyneema® brand yarns.

It is surprising that the process according to the invention results in yarn with improved tensile properties, because processes for making HPPE multifilament yarn comprising a step with a certain draw ratio, also referred to as stretch ratio, applied to filaments in the solution or fluid state ($DR_{fluid}$) have already been described in numerous publications. For example, in EP 0472114 B1 a process is disclosed, wherein a minimum draw ratio $DR_{fluid}$ of at least 3 is applied in an air-gap of several centimeters. For making 16- or 19-filament yarn from polyethylene of intermediate molar mass (preferably 300-700 kg/mol) a $DR_{fluid}$ of 10-50 is indicated as a preferred range for reaching optimum properties. EP 0200547 B1 suggests that the optimum $DR_{fluid}$ lies in the range from 6 to 200, depending on the concentration of the solution and operating conditions. This publication, however, only discloses spinning of a monofilament in its examples. In EP 0064167 A1 it is concluded, based on a very large number of experiments, that drawing in the air-gap should be minimized, because substantial stretching would be highly detrimental. In addition, EP 0064167 A1 also unambigiously teaches that a long straight capillary is to be preferred over a conical spinhole for increasing polyethylene filament strength. In WO 01/73173 A1 it is indicated that the draw ratio $DR_{fluid}$ is preferably at least 12; but a 16-filament yarn made with a $DR_{fluid}$ of about 34 had tensile properties lower than a yarn made with a $DR_{fluid}$ of about 23. None of these publications discloses or suggests applying a minimum draw ratio $DR_{fluid}$ of 150, resulting from drawing in both the spinhole (by applying a specific spinhole geometry) and the air-gap to make a multifilament yarn with higher strength.

Another advantage of the process according to the invention is that the draw ratio $DR_{sp}$ can be set by choosing the geometry of the spinholes, which can be much better controlled than drawing in an air-gap. A further advantage is that the temperature during drawing in the spinholes can be better controlled than in the air-gap, which further reduces differences in processing conditions between filaments and with time. It is known that even small differences in the temperature of a polyethylene solution will strongly affect its rheological properties, and thus drawing behaviour. Still a further advantage is that a larger air-gap can be applied, which is less critical to small fluctuations, for example resulting from movement of the surface of the quench bath. A distinct advantage of the process of the invention is thus an improved processing stability, and more consistency in properties between and along filaments. These advantages become more apparent with increasing number of filaments that are being spun. Preferably, the number of filaments in the yarn is at least 10, 50, 100, 150, 200, 300, 375 or even at least 450. For practical reasons, handling during spinning and drawing becoming increasingly difficult, the number of filaments is preferably at most about 5000.

A spinplate is also called spinneret in the art, and contains multiple spinholes, also called orifices, dies, apertures, capillaries or channels. The number of spinholes determines the maximum number of filaments in as-spun yarn. The spinhole has certain geometry in length and transverse directions, and is preferably of circular cross-section to result in highest strength, but also other shapes are possible, if other forms of filaments are desired. Within the context of the present invention the diameter is meant to be the effective diameter; that is for non-circular or irregularly shaped spinholes the largest distance between an imaginary line connecting the outer boundaries.

Within the context of the present invention, a draw ratio of greater than 1 in a spinhole is applied, if the polyethylene chains in the solution are oriented as a result of an elongational flow field in the spinhole and the orientation so obtained is not subsequently substantially lost as a result of relaxation processes (occurring in the spinhole). Such molecular orientation, and thus a draw ratio greater than 1 results if the solution flows through a spinhole having a geometry comprising a contraction zone, more specifically in the process according to the invention a zone with a gradual decrease in diameter from diameter $D_0$ to $D_n$ with a cone angle in the range 8-75°, and optionally comprising a zone of constant diameter $D_n$ downstream of a contraction zone, with a length/diameter ratio $L_n/D_n$ of at most 25. Downstream is understood to mean after the contraction zone in the direction of the flowing solution, that is more to the exit side of the spinplate. If the length of a zone with constant diameter is above $25D_n$, molecular orientation introduced in the contraction zone would be substantially lost again; that is there would be no effective orientation or drawing. The draw ratio in such case is defined as $DR_{sp}=1$.

With cone angle is meant the maximum angle between the tangents of opposite wall surfaces in the contraction zone. For example, for a conical or tapered contraction the angle between the tangents is a constant, i.e. the cone angle; for a so-called trumpet type of contraction zone the angle between the tangents will decrease with decreasing diameter; whereas for a wineglass type of contraction zone the angle between the tangents will pass through a maximum value.

A higher cone angle induces more elongational flow, but if the cone angle is greater than 75° flow instabilities like turbulence may disturb the desired elongational orientation of the molecules. Preferably, the cone angle is therefore at most 70°, at most 65°, at most 60°, at most 50°, more preferably at most 45°. With decreasing cone angle orienting the polymer molecules becomes less effective, and very small angles would result in very long spinholes. Preferably, the cone angle is thus from at least 10, more preferably at least 12°, or even at least 15°.

The draw ratio in the spinhole is represented by the ratio of the solution flow speeds at the initial diameter or cross-section and the final diameter of the spinhole; which is equivalent to the ratio of the respective cross-sectional areas, or the ratio between the square of the initial and final diameters in case of cylindrical holes, that is $DR_{sp}=(D_0/D_n)^2$.

Preferably, the draw ratio in the spinholes is at least 2, 5, 10, 15, 20, 25, 30, 35, 40, 45 or even at least 50, because extent and conditions of drawing can be well controlled in the spinholes. In addition, a higher draw ratio in the spinhole, with constant draw ratio in the air-gap, has been found to result in higher tensile strength of the yarn obtained. In a special embodiment, the $DR_{sp}$ is larger than $DR_{ag}$ for the same reason.

The spinhole further comprises a zone of constant diameter $D_n$ downstream of a contraction zone, this zone having a length/diameter ratio $L_n/D_n$ of at most 25. The length of this zone can also be 0; such a zone need not be present in the spinhole. The advantage of the presence of this constant diameter zone is a further improved stability of the spinning process. On the other hand, its length should be limited in order that the molecular orientation introduced in the contraction zone is not substantially lost. Therefore, the ratio $L_n/D_n$ is preferably at most 20, at most 15, 10, or even at most 5.

The final diameter of the spinhole may vary considerably, depending on total draw ratio applied in the process and desired final filament thickness. A suitable range is from 0.2 to 5 mm, preferably the final diameter is from 0.3 to 2 mm.

The spinholes may also contain more than one contraction zone, each optionally followed by a zone of constant diameter. In such case similar features relate to each zone as discussed above.

In a special embodiment of the process according to the invention, the spinholes in the spinplate further comprise an inflow zone of constant diameter of at least $D_0$, and of length $L_0$ with a ratio $L_0/D_0$ of at least 5. The advantage of such zone is that the polymer molecules in the solution can at least partly relax before entering the contraction zone, such that pre-orientation originating from flow fields further upstream in the process will disappear or at least significantly diminish. This is especially advantageous in case of a high number of spinholes, requiring complex feed channels to the spinplate, which may result in quite different flow histories and degrees of pre-orientation per spinhole; and thus in differences in drawing behaviour of filaments, and in differences in properties between filaments in the yarn. The longer this inflow zone, the more relaxation can occur, and the better inter filament homogeneity or yarn uniformity. Therefore, the inflow zone preferably has a $L_0/D_0$ of at least 10, 15, 20, or even at least 25. It should be noted that the flow speed in this zone is significantly lower than after passing the contraction zone, and for relaxation to occur a relatively small $L_0/D_0$ suffices. Above a certain length, further increase has hardly any effect, but such a long inflow zone would result in very thick spinplates that are more difficult to make and handle. The inflow zone thus preferably has a $L_0/D_0$ of at most 100, or at most 75, or 50. The optimum length depends on factors like molar mass of polyethylene, concentration of the solution, and flow speeds.

In a preferred embodiment of the process according to the invention a spinplate comprising at least 10 cylindrical spinholes having a inflow zone of constant diameter $D_0$ with $L_0/D_0$ at least 10, at least one contraction zone with cone angle in the range 10-60°, a downstream zone of constant diameter $D_n$ with $L_n/D_n$ at most 15, and $(D_0/D_n)^2$ of at least 5 is applied, but also any other combination of indicated preferred embodiments is possible.

In the process according to the invention the fluid filaments can be further drawn upon leaving the spinhole, by applying a higher pick-up rate after cooling the filaments, than the flow rate upon leaving the spinhole. This stretching applied before solidification upon cooling is called the draw ratio in the air-gap $DR_{ag}$, and is in prior art also referred to as draw down. The $DR_{ag}$ can be 1.0 if the pick-up rates equals the flow rate, but the draw ratio is preferably greater than 1 to keep the filaments under sufficient tension and to prevent relaxation. Preferably, $DR_{ag}$ is optimised in combination with the applied $DR_{sp}$ to reach a certain $DR_{fluid}$. Preferably, the draw ratio in the air-gap is at least 2, 5, or 10. The dimension of the air-gap, that is the distance from the exit of the spinplate to the surface of the quench bath, appears not to be very critical, although it is preferably kept constant and the same for all filaments, and can be from some mm to several cm. If the air-gap is too long, molecular relaxation processes may annul part of the orientation obtained. Preferably, the air-gap is of about 5-50 mm length.

The draw ratio $DR_{fluid}$, being $DR_{sp}*DR_{ag}$, that is applied to fluid filaments is at least 150, preferably at least 200, 250, or even at least 300. It is found that such a high draw ratio applied to fluid filaments results in improved drawability of the gel and dried filaments ($DR_{solid}$), and/or in improved properties, like tensile strength of the resulting yarn. This is also synonymous with improved processing stability of the process, since it reduces the chance that a filament is over-stressed during (semi-)solid state drawing at a certain draw ratio closely below the maximum, and thus reduces frequency of filament breakage. This is a surprising result, since experiments in prior art publications like EP 0064167 A1 or WO 01/73173 A1 indicate that increasing the $DR_{fluid}$ results in a lower draw ratio that can subsequently be applied to the solid filaments, and in lower tensile properties of the yarn.

The ultra-high molar mass polyethylene applied in the process according to the invention has an intrinsic viscosity (IV, as measured on solution in decalin at 135° C.) of between about 8 and 40 dl/g, preferably between 10 and 30, or 12 and 28, more preferably between 15 and 25 dl/g, to provide a balance between processability of the solution to be spun and mechanical properties of the obtained filaments. Intrinsic viscosity is a measure for molar mass (also called molecular weight) that can more easily be determined than actual molar mass parameters like $M_n$ and $M_w$. There are several empirical relations between IV and $M_w$, but such relation is dependent on molar mass distribution. Based on the equation $M_w=5.37*10^4 [IV]^{1.37}$ (see EP 0504954 A1) an IV of 4 or 8 dl/g would be equivalent to $M_w$ of about 360 or 930 kg/mol, respectively. It is well known that during processing of a polymer at elevated temperature generally some chain scission occurs, leading to a lower molar mass of the product obtained versus that of the starting polymer. It is found that upon gel spinning of UHPE an IV drop of about 1-3 g/dl may occur, depending on starting molar mass and processing conditions.

Preferably, the UHPE is a linear polyethylene with less than one branch per 100 carbon atoms, and preferably less than one branch per 300 carbon atoms; a branch or side chain or chain branch usually containing at least 10 carbon atoms. The linear polyethylene may further contain up to 5 mol % of one or more comonomers, such as alkenes like propylene, butene, pentene, 4-methylpentene or octene.

In a preferred embodiment, the UHPE contains a small amount, preferably at least 0.2, or at least 0.3 per 1000 carbon atoms, of relatively small groups as pending side groups, preferably a C1-C4 alkyl group. It is found that by applying a polymer containing a certain amount of such groups results in yarns having an advantageous combination of high strength and further improved creep behaviour. Too large a side group, or too high an amount of side groups, however, negatively affects the processing and especially the drawing behaviour of the filaments. For this reason, the UHPE preferably contains methyl or ethyl side groups, more preferably methyl side groups. The amount of side groups is preferably at most 20, more preferably at most 10, 5 or at most 3 per 1000 carbon atoms.

The UHPE that is applied in the process according to the invention may further contain small amounts, generally less than 5 mass %, preferably less than 3 mass % of customary additives, such as anti-oxidants, thermal stabilizers, colorants, flow promoters, etc. The UHPE can be a single polymer grade, but also a mixture of two or more different polyethylene grades, e.g. differing in IV or molar mass distribution, and/or type and number of comonomers or side groups.

In the process according to the invention any of the known solvents suitable for gel spinning of UHPE can be used as solvent for making the polyethylene solution, for example paraffin wax, paraffin oil or mineral oil, kerosenes, decalin, tetralin, or a mixture thereof. It is found that the present process is especially advantageous for relatively volatile solvents, preferably solvents having a boiling point at atmospheric conditions of less than 275° C., more preferably less than 250 or 225° C. Suitable examples include decalin, tetralin, and several kerosene grades. The solution of UHPE in solvent can be made using known methods. Preferably, a twin-screw extruder is applied to make a homogeneous solution from a UHPE/solvent slurry. The solution is preferably fed to the spinplate at constant flow rate with metering pumps. The concentration of the UHPE solution is between 3 and 25 mass %, with a lower concentration being preferred the higher the molar mass of the polyethylene is. Preferably, the concentration is between 3 and 15 mass % for UHPE with IV in the range 15-25 dl/g.

The UHPE solution is preferably of substantially constant composition over time, because this further improves processing stability and results in yarn of more constant quality over time. With substantially constant composition it is meant that parameters like UHPE chemical composition and molar mass, and concentration of UHPE in the solution vary only within a certain range around a chosen value.

Cooling of the fluid filaments into solvent-containing gel filaments may be performed with a gas flow, or by quenching the filament in a liquid cooling bath after passing an air-gap, the bath preferably containing a non-solvent for the UHPE solution. If gas cooling is applied, the air-gap is the length in air before the filaments are solidified. Preferably a liquid quench-bath is applied in combination with an air-gap, the advantage being that drawing conditions are better defined and controlled than by gas cooling. Although called air-gap, the atmosphere can be different than air; e.g. as a result of an inert gas like nitrogen flowing, or as a result of solvent evaporating from filaments. Preferable, there is no forced gas flow, or only of low flow rate. In a preferred embodiment, the filaments are quenched in a bath containing a cooling liquid, which liquid is not miscible with the solvent, the temperature of which is controlled, and which flows along the filaments at least at the location where the fluid filaments enter the quench bath.

Solvent removal can be performed by known methods, for example by evaporating a relatively volatile solvent, by using an extraction liquid, or by a combination of both methods.

The process for making a polyethylene yarn according to the invention further comprises, in addition to drawing the solution filaments, drawing the filaments in at least one drawing step performed on the semi-solid or gel filaments and/or on solid filaments after cooling and at least partial removal of solvent, with a draw ratio of at least 4. Preferably, drawing is performed in more than two steps, and preferably at different temperatures with an increasing profile between about 120 and 155° C. A 3-step draw ratio applied on (semi-) solid filaments is represented as $DR_{solid} = DR_{solid\,1} * DR_{solid\,2} * DR_{solid\,3}$; i.e. it is composed of the draw ratios applied in each drawing step.

It is found that a draw ratio $DR_{solid}$ of upto about 35 can be applied, to reach the highest tensile properties of the yarn obtainable for a given $DR_{fluid}$. As a result of improved drawability and strength of partly drawn filaments in the process according to the invention, relatively high draw ratios, preferably in the range 5-30, may be applied without frequent filament breakage occurring, also depending on the applied draw ratio on fluid filaments. The process according to the invention thus results in multifilament HPPE yarn not only showing higher tensile strength than known multifilament yarns, but also less fluffing (resulting from the presence of broken filaments); especially if draw ratios have been optimised.

In a special embodiment according to the invention, a 3-15 mass % solution of linear UHPE of IV 15-25 dl/g is spun through a spinplate containing at least 10 spinholes into an air-gap, the spinholes comprising at least one contraction zone with a cone angle in the range 10-60° and comprising a zone of constant diameter $D_n$ with a length/diameter ratio $L_n/D_n$ smaller than 10 downstream of the contraction zone, while applying a fluid draw ratio $DR_{fluid} = DR_{sp} * DR_{ag}$ of at least 200 and a draw ratio $DR_{solid}$ of between 5 and 30; but also other combinations of said parameter settings provide good results.

The process according to the invention may further comprise additional steps known in the art, like for example applying a spin finish or sizing agent to the yarn.

The invention further relates to a spinplate comprising at least 5 spinholes of geometry and preferred features as defined and described above. The advantage of said spinplate is that, when applied in a process for making high-performance polyethylene multifilament yarn it enables a high degree of drawing on fluid filaments and a stable spinning process, resulting in yarn of increased strength and with high consistency in properties between individual filaments.

The invention further relates to a HPPE multifilament yarn that is obtainable by the process according to the invention, the yarn showing higher tensile strength than any known HPPE yarn containing at least 5 filaments. More specifically, the invention relates to a HPPE multifilament yarn made from linear UHPE of IV 8-40 dl/g, containing n filaments and having a tensile strength of at least $f*(n^{-0.0065})$ GPa, wherein factor f is at least 5.8 and n is at least 5. Preferred embodiments of the yarn according to the invention are based on UHPE grades as described above. Preferably, the yarn has a tensile strength obeying said formula wherein f is at least 6.0, 6.2 or even at least 6.4. Considering that the maximum theoretical strength of a filament is by some authors indicated to be about 10 GPa, factor f would be 10 at most, or even at most 9 or 8.

The HPPE multifilament yarn according to the invention is further characterized by a total enthalpy of non-reversible transitions as measured by temperature-modulated differential scanning calorimetry (TMDSC) of at least 200 J/g. In addition, or alternatively, the HPPE multifilament yarn according to the invention is further characterized by a peak in the non-reversible TMDSC curve, called hereafter non-reversible peak, with a maximum at about 152° C. as measured by TMDSC having an enthalpy of at least 35 J/g, preferably at least 38 or 40 J/g. Although these TMDSC results are not yet fully understood and the inventors do not wish to be bound to any theory, it is presently believed that especially the non-reversible peak at 152° C. correlates to oriented crystallisation of the polyethylene molecules promoted by the spinning process of the invention, and resulting in improved mechanical properties.

The HPPE multifilament yarn according to the invention is further found to show favourable creep resistance, for example expressed in a creep rate as determined on yarn at 70° C. with a load of 600 MPa of at most $5*10^{-6}$ $s^{-1}$, preferably at most $4*10^{-6}$ $s^{-1}$. A HPPE multifilament yarn according to the invention made from a linear UHPE with 0.2-10 C1-C4 alkyl groups per 1000 C atoms shows even better resistance to creep in combination with high strength; that is it has a creep rate as determined on yarn at 70° C. with a load of 600 MPa of at most $3*10^{-6}$ $s^{-1}$, preferably at most $2*10^{-6}$ $s^{-1}$ or even $1*10^{-6}$ $s^{-1}$.

Preferably, the number of filaments in the yarn according to the invention is at least 10, 50, 100, 150, 200, 300, 375 or even at least 450.

Preferably, the said yarn is an as-spun or as-produced yarn; meaning the yarn is the direct product of a spinning and drawing process, and is not made by assembling separately produced yarns containing less filaments. Of course, the as-produced yarn according to the invention can further be assembled into yarns, or ropes etc, of higher titer or linear density.

Such high-strength yarn is very useful for various applications, like making of heavy-duty ropes and cables, or for making ballistic-resistant composites offering improved protection level, or reduced weight. Yarn of relatively low titer, containing for example from 5 to 300 filaments, but of extremely high strength is, for example, very suited for making high-strength surgical sutures and cables, or other medical implants. For medical applications the amount of other components or foreign materials in the yarn is very important, in addition to its mechanical properties. The invention therefore also specifically relates to a HPPE multifilament yarn according to the invention containing less than 150 ppm of residual solvent, specifically of solvent having a boiling point at atmospheric conditions of less than 275° C., preferably containing less than 100, 75, or even less than 50 ppm of solvent, and to medical implants containing such yarn.

The invention specifically relates to a HPPE multifilament yarn containing at least 20 filaments, the yarn being made from UHPE of IV 8-40 dl/g and having a tensile strength of at least $f*(n^{-0.065})$ GPa, with n at least 20 and f at least 5.8. Especially for making ropes, multifilament yarn of such high strength, which also shows an elongation at break of more than about 2.5% is advantageous, because of higher strength efficiency of such ropes. The invention therefore specifically relates to a HPPE multifilament yarn containing at least n filaments made from UHPE of IV 8-40 dl/g, which yarn has a tensile strength of at least $f*(n^{-0.065})$ GPa with n at least 200, preferably at least 300 or 375 and with f at least 5.8, a creep rate as determined at 70° C. with a load of 600 MPa of at most $5*10^{-6}$ $s^{-1}$, and an elongation at break of at least 2.8%.

The invention further relates to various semi-finished and end-use articles containing the high-performance polyethylene multi-filament yarn according to the invention, or a high-performance polyethylene multi-filament yarn obtainable by the process according to the invention. Examples of such articles include various ropes and cords, fishing nets, sports equipment, medical implants like suture and cables, and ballistic-resistant composites. In most of these applications the tensile strength of the yarn is an essential parameter determining performance of the article.

Ropes especially include heavy-duty ropes for application in marine and offshore operations, like anchor handling, seismic operations, mooring of drilling rigs and production platforms, and towing. Preferably, such ropes contain at least 50 mass % of the yarn according to the invention, more preferably at least 75, or even 90 mass %. Most preferably, the rope consists essentially of HPPE yarn according to the invention. Such products also show improved performance, like reduced creep and longer time to rupture under continuous loading conditions, in addition to higher strength. Products containing high amounts of HPPE yarn have a low relative density; possibly lower than water, which is an advantage in marine and offshore applications.

The invention further relates to a multi-layer ballistic-resistant assembly containing a plurality of mono-layers comprising HPPE yarn according to the invention, and to ballistic-resistant articles comprising such an assembly. The HPPE yarn can be present in various forms in a mono-layer, including woven and non-woven fabrics. Preferably, the mono-layers contain uni-directionally oriented HPPE filaments; with the fibre direction in each mono-layer being rotated with respect to the fibre direction in an adjacent mono-layer. The mono-layers may further comprise a binder material, basically to hold the filaments together. The binder material can have been applied by various techniques; for example as a film, as a transverse bonding strip or fibres (transverse with respect to the uni-directional filaments), or by impregnating and/or embedding the filaments with a matrix, e.g. with a solution or dispersion of matrix material in a liquid. The amount of binder material is preferably less than 30 mass % based on the mass of the layer, more preferably less than 20 or 15 mass %. The mono-layers may further comprise small amounts of auxiliary components, and may comprise other filaments. Preferably the mono-layers only comprise HPPE filaments as reinforcing fibres. Such mono-layers are therefore also referred to as mono-layers consisting essentially of HPPE filaments.

The multi-layer ballistic-resistant assembly can also be an assembly of at least two preformed sheet layers, a sheet layer comprising at least two mono-layers comprising high-performance fibres and a binder material, and optionally other layers, like a film or fabric; that have been consolidated or attached to each other. Such multi-layer ballistic-resistant assemblies or panels, and their manufacture are known in the art, for example from U.S. Pat. No. 4,916,000, U.S. Pat. No. 4,623,574, EP 0705162 A1 or EP 0833742 A1.

For so-called hard ballistic applications like vehicle armouring, rigid panels that have been (compression-) moulded from a plurality of mono-layers containing HPPE yarn are generally applied. For soft ballistic applications like body armour, flexible panels assembled from a plurality of mono-layers containing HPPE yarn, e.g. by stacking mono-layers or preformed sheets and securing the stack by for example stitching at the corners or around the edges, or by placing inside an envelope, are preferred.

A multi-layer ballistic-resistant assembly containing mono-layers consisting essentially of HPPE yarn according to the invention shows surprisingly good anti-ballistic properties, exceeding the performance of known assemblies or panels. It is for example found that a flexible assembly that fulfils the NIJ II requirements (stopping of a 9 mm Parabellum FMJ (full metal jacket) bullet of 8.0 g with impact speed of 367 m/s, and a 0.357 Magnum JSP (jacketed soft point) bullet of 10.2 g at a speed of 436 m/s), has an areal density about 25% or more lower than that of a state-of-the-art panel. A reduced weight is a distinct advantage in both personal protection as in vehicle armouring and the like.

The invention more specifically relates to a ballistic-resistant assembly comprising a plurality of mono-layers consisting essentially of HPPE multifilament yarn, the assembly having an areal density (AD) of at least 1.5 kg/m² and a specific energy absorption (SEA) of at least 300 J·m²/kg as measured against a 9*19 mm FMJ Parabellum bullet according to a test procedure based on Stanag 2920. Preferably, the assembly has a SEA of at least 325, or at least 350 J·m²/kg. Areal density is expressed in mass per surface area, and is also referred to as areal mass or areal weight.

The invention further relates to a ballistic-resistant moulded panel comprising a plurality of mono-layers consisting essentially of HPPE multifilament yarn, the panel having a specific energy absorption (SEA) of at least 165 J·m²/kg as measured against an AK-47 bullet according to a test procedure based on Stanag 2920. Preferably, the panel has a SEA of at least 170, or at least 175 J·m²/kg.

The invention is further elucidated by the following examples and comparative experiments.

Methods

IV: the Intrinsic Viscosity is determined according to method PTC-179 (Hercules Inc. Rev. Apr. 29, 1982) at 135° C. in decalin, the dissolution time being 16 hours, with DBPC as anti-oxidant in an amount of 2 g/l solution, by extrapolating the viscosity as measured at different concentrations to zero concentration;

Side chains: the number of side chains in a UHPE sample is determined by FTIR on a 2 mm thick compression moulded film, by quantifying the absorption at 1375 cm$^{-1}$ using a calibration curve based on NMR measurements (as in e.g. EP 0269151);

Tensile properties: tensile strength (or strength), tensile modulus (or modulus) and elongation at break (or eab) are defined and determined on multifilament yarns with a procedure in accordance with ASTM D885M, using a nominal gauge length of the fibre of 500 mm, a crosshead speed of 50%/min and Instron 2714 clamps, of type Fibre Grip D5618C. On the basis of the measured stress-strain curve the modulus is determined as the gradient between 0.3 and 1% strain. For calculation of the modulus and strength, the tensile forces measured are divided by the titre, as determined by weighing 10 meters of fibre; values in GPa are calculated assuming a density of 0.97 g/cm³;

Temperature Modulated Differential Scanning calorimetry (TMDSC) experiments were carried out on a TA Instruments Heatflux DSC 2920 equipped with a Refrigerated Cooling System (RCS). Helium was used as purge gas (35 ml/min). Aluminum crucibles (Perkin Elmer, robotic pans) were used as sample holders. Fibres were cut to a length between 1 and 2 mm before analysis. Calibration procedures included temperature calibration water and Indium; enthalpy calibration with Indium; and heat capacity calibration with Standard Reference Material1484 Linear Polyethylene Cp at 150° C.=2.57 J/° C. (National Bureau of Standards Washington D.C.).

The applied measuring conditions are based on a publication by G. Hohne for UHPE powder (Thermochimica Acta 396, 2003, 97-108). The measuring method included equilibration at 80° C.; modulation+/−0.20° C. every 80 seconds; and scanning at a rate of 1.00° C./min to 180° C. TMDSC curves for reversible and non-reversible transitions were calculated from measured total heat flow and complex heat capacity. Reported values for peak temperatures and enthalpies of various peaks were calculated with standard soft-ware assuming a continuous base-line; for peaks having a (broad) maximum below 140° C., a maximum in the range 140-144 (142)° C., and in the range 150-153 (152)° C.

Creep properties of yarns were determined with an experimental set-up comprising a temperature-controlled chamber, sample fixations with a cylindrical steel rod having a smooth surface, and an automated system to load the sample, and to monitor the displacement of the applied weight versus time. The ends of a yarn sample of suitable length, from 200-1000 mm depending on anticipated elongation, is wound several times around the steel rod and fixated with knots. The sample is then placed in the creep chamber, and after preloading during 10-30 s and subsequent relaxation, the measurement is started. The observed elongation versus time typically shows three regimes: after an initially relatively fast elongation a plateau in creep rate is reached (regime 2, also called steady state creep). In the third regime, molecular chain scission effects start to play a role in addition to plastic creep, finally resulting in yarn breakage. The reported creep values relate to regime 2, as calculated from experiments performed at 70° C. and with 600 MPa load on the yarn. Creep life time values were determined as the transfer from regime 2 to regime.

Ballistic performance: V50 and SEA of composite panels were determined at 21° C. with test procedures according to Stanag 2920, using 9 mm*19 mm FMJ Parabellum bullets (from Dynamit Nobel); Fragment Simulating Projectiles (FSP) of 1.1 gram and 5.38 mm; or 7.62*39 mm AK-47 Mild Steel Core bullets of 8.0 g (from Conjoy, UK). After conditioning at 21° C. and 65% relative humidity during at least 16 hours, an assembly of layers was fixed using flexible straps on a support filled with Roma Plastilin backing material, which was preconditioned at 35° C. In case of AK-47 ammunition, panels were clamped onto a steel frame and fired at without backing.

Examples 1-2

A 6 mass % solution of a UHPE homopolymer having less than 0.3 side groups per 1000 per carbon atoms and an IV of 27.0 dl/g in decalin, containing a ratio of cis/trans isomers of between 38/62 and 42/58, was made, and extruded with a 25 mm twin screw extruder equipped with a gear-pump at a temperature setting of 180° C. through a spinplate having 24 spinholes into a nitrogen atmosphere with a rate of 1.0 g/min per hole. The spinholes had an initial cylindrical channel of 3.0 mm diameter and L/D of 18, followed by a conical contraction with cone angle 45° into a cylindrical channel of 1.0 mm diameter and L/D of 10. The solution filaments were cooled in a water bath kept at about 35° C. and with a water flow rate of about 5 cm/s perpendicular to the filaments entering the bath, and taken-up at such rate that a draw ratio of 15 was applied to the as-spun filaments in the air-gap of 15 mm. The filaments subsequently entered an oven at 130° C. The filaments were further stretched by applying a draw ratio of about 4, during which process the decalin evaporated from the filaments. The total draw ratio $DR_{overall}$ ($=DR_{fluid}*DR_{solid}$) amounted 1440. The yarn thus obtained had a tensile strength of 5.2 GPa and a modulus of 202 GPa. Relevant data is shown in Table 1.

In Example 2 the experiment was repeated, be it that a draw ratio in the semi-solid state of 5 was applied. As a result of the higher draw ratio, also higher tensile properties were found.

Comparative Experiment A

In this experiment the draw ratio in the air-gap was lowered, resulting in a $DR_{fluid}$ of 135. The measured tensile strength was significantly lower than for higher draw ratio.

Example 3

This experiment is performed analogously to the foregoing, with following modifications: the spinplate has an inflow channel of diameter 4.5 mm and L/D=10, a contraction zone with cone angle 20°, and subsequent channel of diameter 0.3 mm and L/D of 5, resulting in a $DR_{sp}$ of 225; the draw ratio in the air-gap is about 1.01 by matching take-up speed with flow speed. With the draw ratio applied to the solidified filaments set at 5, the resulting yarn shows extremely high tensile strength and modulus.

Comparative Experiments B-C

In these experiments a solution of a UHPE polymer having less than 0.3 side groups per 1000 per carbon atoms and an IV of 19.8 dl/g in decalin was extruded with a 40 mm twin screw extruder equipped with a gear-pump at a temperature setting of 180° C. through a spinplate having 195 spinholes into an air-gap with a rate of 2.2 g/min per hole. The spinholes had the same geometry as in Ex 1-2, but with cone angle 60°. In exp. B an 8 mass % solution was used, in exp. C 9 mass %. The water in the quench bath was kept at 30-40° C., and had a flow rate of about 3 cm/s near the filaments. Solid-state drawing was performed in two steps, first with a temperature gradient of about 110-140° C. and than at about 151° C. The draw ratio in the air-gap could not be increased too much without processing instabilities occurring (filament breakage), unlike in e.g. Ex. 1, which may be related to the lower molar mass UHPE used. The resulting yarn had a strength comparable with known yarns, see Table 1 and FIG. 2.

Examples 4-5

The same spinning and drawing equipment and conditions as in Comp. Exp. B-C were used, but with a spinplate having an inflow channel of diameter 3.5 mm and L/D=18, a contraction zone with cone angle 60°, and subsequent channel of diameter 1.0 mm and L/D of 10, resulting in a $DR_{sp}$ of 12.25. The spin rate was 1.7 g/min per hole. The draw ratio in the air-gap could be increased, resulting in stable production of very high strength yarn, see Table 1 and FIG. 2.

Example 6

Example 4 was repeated with a spinplate having 195 holes of similar geometry, but with a cone angle of 30°.

Comparative Experiments D-F

Analogously to Comparative experiments B-C a yarn was made, but with a spinplate containing 390 spinholes of same geometry. HDPE solution was 8, 8 and 9 mass % respectively. The experimental results were also highly comparable; the yarn showing slightly lower tensile strength as expected for the higher number of filaments.

Examples 7-10 and Comparative Experiment G

Using the same set-up and conditions as in comp. Exp. D, yarns were spun applying a spinplate having 390 spinholes of geometry as in Ex 4-5. In Ex. 10 the spinrate was lowered to 1.7 g/min per hole. Again, a high draw ratio could be applied to the fluid filaments, resulting in very good tensile properties; see Table 1 and FIG. 2. If the $DR_{fl}$ was decreased by applying a relatively small draw ratio in the air-gap, tensile strength dropped significantly (Comp. Exp. G).

Examples 11-12

Multifilaments yarns were spun from a decalin solution containing 8 mass % of UHPE of IV 19.8 dl/g, using a 130 mm twin-screw extruder equipped with a gear-pump through spinplates containing 588 spinholes having an inflow zone of diameter 3.5 mm and L/D of 18, a conical contraction zone with cone angle 60°, and subsequent capillary with diameter 0.8 mm and L/D 10. The draw ratio in the spinholes was thus 19.1; the draw ratio in the air-gap was 16.2 and 18.1 (at spinrates 2.2 and 2.0 g/min per spinhole). Water flow rate in the cooling bath was about 6 cm/s. The tensile properties of the yarns are in agreement with yarns produced under similar conditions but containing less filaments (see Table 1 and FIG. 2).

Example 13

The experiment of Example 11 was repeated, but with similar spinplates containing 1176 spinholes. Multifilament yarns containing 1176 filaments having very high tensile strength could be produced with high processing stability.

Comparative Experiment H

The experiment of Comp. Exp. F was repeated, but with the spinplate containing 780 spinholes; and essentially the same results.

Examples 14-16

Using the experimental set-up and conditions of Ex. 4, yarns were spun from a 7 mass % solution of UHPE of IV 21.4 and less than 0.3 side groups per 1000 per carbon atoms, with a spinrate of 1.7 g/min per spinhole. The tensile strength of the yarns obtained were somewhat higher than of comparable products made from lower molar mass UHPE.

Examples 17-20

An 8 mass % solution of UHPE having 0.65 methyl sidegroups per 1000 C atoms and IV of 23 dl/g was spun into yarn, using a spinplate containing 390 spinholes of geometry as in Ex. 4, but with a cone angle of 30°. Other spinning and drawing conditions were the same, but the draw ratio in the air-gap was varied. The strength of the yarns obtained is comparable to the results with polymer containing very little propylene as comonomer, but the creep properties are significantly improved; see Tables 1 and 2.

Comparative Experiments I-J

Analogously to Ex. 17-20 yarns were made, but with lower draw ratio in air gap and $DR_{fluid}$, resulting in lower strength.

Figure 2:
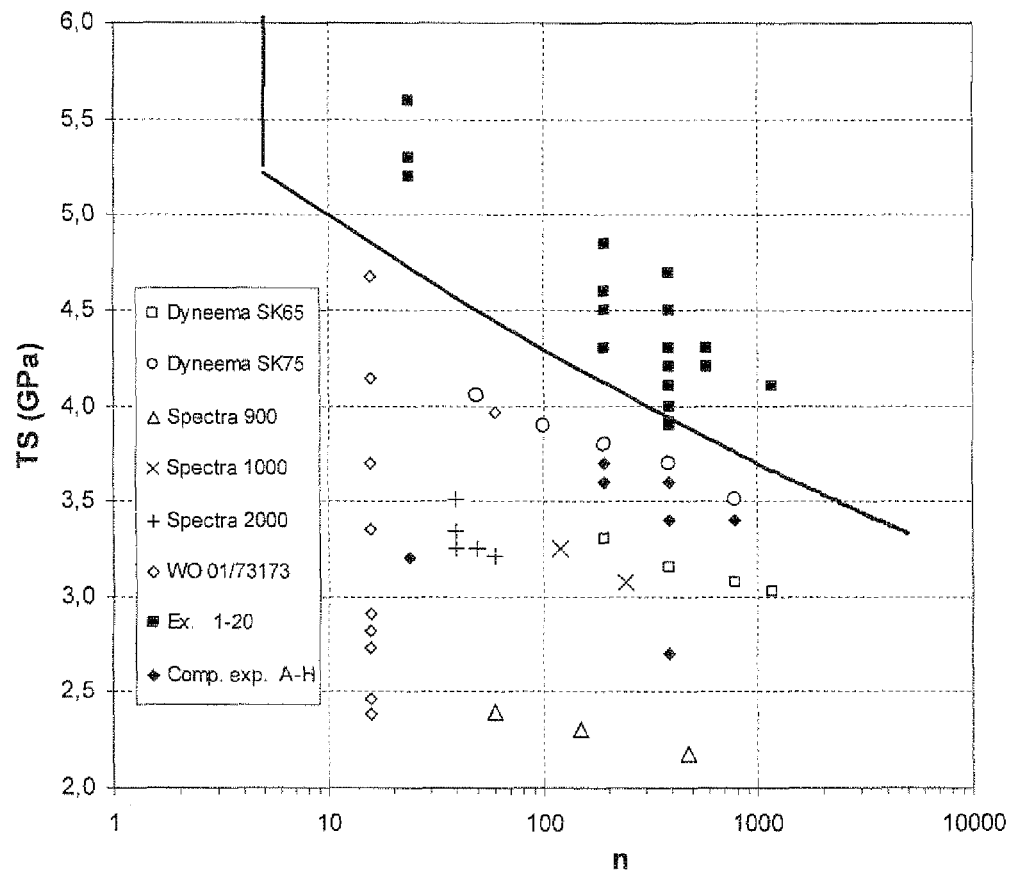
FIG. 2 is a plot of TS versus the number of filaments in a yarn for Examples 1-201 comparison to Comparative Experiments A-H and the data for the commercially available HPPE yarns of FIG. 1.

In FIG. 2 the tensile strengths as measured in all above experiments have been plotted versus the logarithm of the number of filaments in the respective yarn. Also included are data points from the experiments reported in WO 01/73173, as well as those from FIG. 1 on commercial samples. It is clearly seen that the Examples 1-20 display higher strength than the known yarns and yarns made in Comp. Exp. A-H, and that these strength values are at least $5.8*(n^{-0.065})$ GPa with n at least 5; which formula is represented in FIG. 2 by the bold line.

In Table 2 results of creep measurements performed on some selected samples at 70° C. with a load of 600 MPa are summarized. It can be concluded that the yarns made with higher draw ratio applied to fluid filaments, and showing higher tensile properties, also show better resistance to creep: about 3-fold improvement in creep rate is found for a yarn made from the same polymer (Ex. 16 vs Comp. Ex. H), and about 10-fold improvement for a yarn made from a UHPE polymer with small amount of propylene as comonomer (Ex. 20).

A number of yarn samples was studied with TMDSC, results are presented in Table 3. The various samples do not appear to show a specific trend in enthalpy effects for reversible transitions, but it can be concluded that yarns according to the invention show higher total enthalpy values for non-reversible transitions, and especially a larger peak with its maximum at about 152° C.

Example 29

The experiment of Example 19 was repeated, but the final drawing step on solid filaments was now performed in two stages, by passing the yarn twice through the oven at lower rate. Instead of a final drawing step with $DR_{solid2}$ of 6.4 now $DR_{solid2}*DR_{solid3}$ of 5*1.7=8.4 was applied. The residence time in the oven this way increased from about 2 minutes to about 6.3 minutes. The yarn obtained had a tensile strength of 4.1 GPa, a modulus of 182 GPa, and a decalin content of 16 ppm.

Example 19 resulted in a yarn with decalin content of 135 ppm. For comparison, the yarn of Comp. G was found to contain about 1150 ppm of decalin, Comp. D 890 ppm and Comp. E 400 ppm decalin; the decrease roughly correlating with the decrease in filament thickness (oven residence time was about constant).

Example 30

Example 29 was repeated, but the final solid-state 2-staged drawing step was now performed under an inert nitrogen atmosphere instead of in air, in order to prevent possible oxidative degradation. The yarn obtained showed improved tensile properties (strength 4.6 GPa and modulus 179 GPa); and very low decalin content (about 18 ppm).

Example 21

The multifilament yarn of Example 13, having a titer of 930 dtex, was used to make a uni-directional (UD) mono-layer by feeding the yarn from several packages from a creel, spreading the filaments, and impregnating the filaments with an aqueous dispersion of Kraton® D1107 stryrene-isoprene-styrene blockcopolymer as matrix material. After drying the UD mono-layer had an areal density of 22.2 g/m² and a matrix content of about 23 mass %. Four (4) of these mono-layers of 40*40 cm size were stacked cross-wise (fibre direction in each layer at an angle of 90° with direction in adjacent layer), a polyethylene film of about 7 g/m² was placed on both sides of the stack, and the package was consolidated by compressing at about 110° C. and about 0.5 MPa. The areal density of this preformed sheet was 103.8 g/m².

A number of these sheets were stacked, and the assembly was stabilized by some stitches at each corner. The ballistic performance of the assembly was tested with 9 mm Parabellum bullets (see above). In Table 4 the results are collected for assemblies with 3 different areal densities.

Examples 22-23

Example 21 was repeated, but the mono-layers now had AD 20.2 g/m² and matrix content 15 mass % (Ex. 22). Ex 23 was made with the yarn of Example 11 of 465 dtex, the mono-layer had AD of 18.4 g/m² and 15 mass % of matrix. More details are given in Table 4.
Comparative Experiment K
Analogously to Ex. 21 assemblies were made from a commercial multifilament HPPE yarn (Dyneema® SK76 1760 dtex), containing 780 filaments and with TS 3.5 GPa. The mono-layer had an AD of 32.8 g/m² and a matrix content of 18 mass %.

Figure 3:
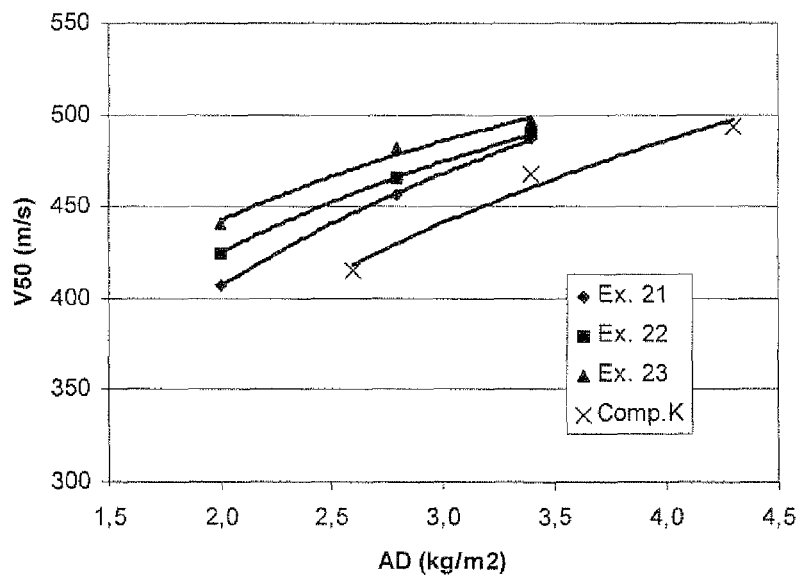
FIG. 3 is a plot of V50 values (m/s) versus areal density of panels made with the yarns of Examples 21-23 in comparison to Comp. ex. K.

From the data in Table 4 it is clear that the panels made with a yarn according to the invention show significantly better ballistic performance in relation to their areal density. In FIG. 3 this is further illustrated by plotting the V50 values, the velocity at which the estimated probability that a bullet will perforate the panel is 50%, versus areal density for Ex. 21-23 and Comp. exp. K.

Example 24

A UD mono-layer was made as in Ex 21 with AD of 37.6 g/m² and matrix content of about 10 mass %. A preformed sheet was made by placing two mono-layers cross-wise with a polyethylene film of 7 g/m² on both sides, and consolidating by compression. The AD hereof was 89.2 g/m².

A number of these sheets were stacked, stabilized with stitches, and tested on anti-ballistic performance as before.

Examples 25-26

Starting from a mono-layer with AD 40.3 g/m² and 15 mass % of matrix, Ex 24 was repeated.

In Ex. 26 the experiment of Ex 24 was repeated, but 4 instead of 2 mono-layers were placed cross-wise and consolidated into a sheet.
Comparative Experiment L
Monolayers and sheet were made as in Comp. Exp. K. The mono-layer had an AD of 58.5 g/m² and a matrix content of 16 mass %.

Figure 4:
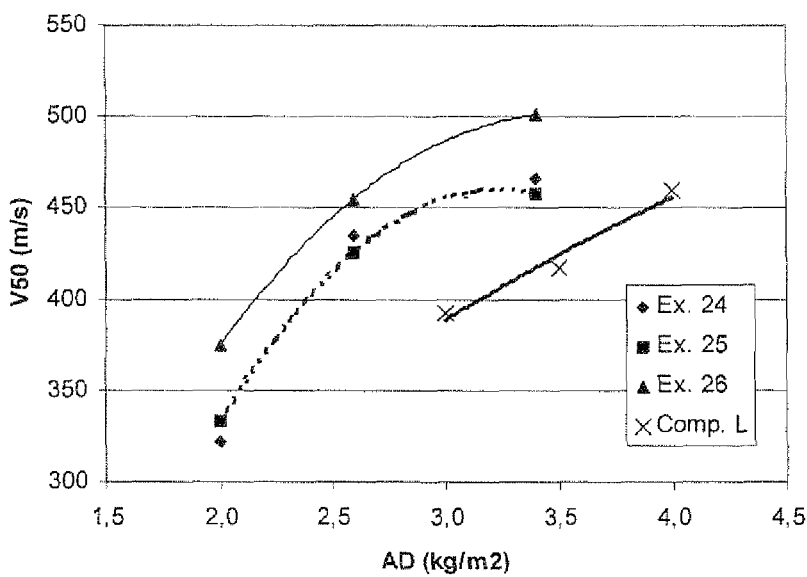
FIG. 4 is a plot of V50 values (m/s) versus areal density of panels made with the yarns of Examples 24-26 in comparison to Comp. exp. L.

The results shown in Table 4 show that also for assembled panels of structure differing form Ex. 21-23, the panels made from yarn according to the invention have significantly better protection level at the same areal density than panels according to the state of the art. In FIG. 4 this is further illustrated by plotting the V50 values versus areal density.

Examples 27

The mono-layers of Example 25 were made into a preformed sheet by placing two layers cross-wise, and consolidating them analogously to the procedure described for Example 21, but without using polyethylene films. Subsequently, 40*40 cm panels of varying weights were compression moulded from stacks of said preformed sheets, by placing a stack between the heated platen of a press, compressing the stack during at least 30 min. at about 6.5 MPa and at 125° C., and cooling under said pressure until the temperature was lower than 60° C.; the panel of 16 kg/m² was compressed during at least 35 min. at 16.5 MPa. In Table 5 the areal densities of the compressed panels, and the results of ballistic testing with different ammunition are presented.

Examples 28

The mono-layers of Example 22 were made into a preformed sheet by placing four layers cross-wise, and consolidating them without using polyethylene films following the procedure described before. Panels were moulded as described for Examples 27; results of ballistic testing are collected in Table 5.
Comparative Experiments M
Analogous to comparative experiment K a monolayer was made containing SK76 fibres and about 18 mass % of matrix, having an AD of 65.5 g/m². Preformed sheets containing 4 of said monolayers were made as before, without cover films; and panels were moulded as described for Examples 27. Results are collected in Table 5.

The data of Table 5 show that panels made from the improved HPPE yarns of the invention show also improved ballistic performance: SEA values are up to about 65% higher; indicating that significant weight savings are possible while offering the same level of protection as known panels.

TABLE 1

| | n | $DR_{sp}$ | $DR_{ag}$ | Air-gap (mm) | $DR_{fluid}$ | $DR_{solid}$ | $DR_{overall}$ | TS (GPa) | Modulus (GPa) | eab (%) |
|---|---|---|---|---|---|---|---|---|---|---|
| Ex 1 | 24 | 9 | 40.0 | 15 | 360 | 4 | 1440 | 5.2 | 202 | |
| Ex 2 | 24 | 9 | 40.0 | 15 | 360 | 5 | 1800 | 5.3 | 208 | |
| comp A | 24 | 9 | 15.0 | 15 | 135 | 5 | 675 | 3.2 | 140 | |
| Ex 3 | 24 | 225 | 1.01 | 5 | 225 | 5 | 1125 | 5.6 | 203 | |
| comp B | 195 | 9 | 4.4 | 15 | 40 | 34 | 1346 | 3.6 | 128 | 2.86 |
| comp C | 195 | 9 | 12 | 20 | 108 | 20 | 2160 | 3.7 | 126 | 3.27 |
| Ex 4 | 195 | 12.25 | 25.2 | 45 | 309 | 24.4 | 7532 | 4.3 | 168 | 3.01 |
| Ex 5 | 195 | 12.25 | 33.5 | 50 | 410 | 25.2 | 10341 | 4.8 | 182 | 2.96 |
| Ex 6 | 195 | 12.25 | 25.2 | 45 | 309 | 25.2 | 7779 | 4.5 | 170 | 3.04 |
| comp D | 390 | 9 | 4.4 | 15 | 40 | 32 | 1267 | 3.4 | 126 | 2.82 |
| comp E | 390 | 9 | 10.2 | 20 | 92 | 33.6 | 3084 | 3.4 | 114 | 2.97 |
| comp F | 390 | 9 | 12 | 20 | 108 | 20 | 2160 | 3.6 | 121 | 3.24 |
| Ex 7 | 390 | 12.25 | 14.6 | 35 | 179 | 24.4 | 4364 | 3.9 | 162 | 3.07 |
| Ex 8 | 390 | 12.25 | 19.4 | 40 | 238 | 18.9 | 4492 | 4.0 | 136 | 3.12 |
| Ex 9 | 390 | 12.25 | 20.0 | 40 | 245 | 21.6 | 5292 | 4.1 | 157 | 3.07 |
| Ex 10 | 390 | 12.25 | 25.2 | 45 | 309 | 24.4 | 7532 | 4.2 | 166 | 2.98 |
| comp G | 390 | 12.25 | 2.2 | 10 | 27 | 28 | 755 | 2.7 | 84 | 2.86 |
| Ex 11 | 588 | 19.1 | 16.2 | 25 | 309 | 25.2 | 7797 | 4.2 | 155 | 2.98 |
| Ex 12 | 588 | 19.1 | 18.1 | 25 | 346 | 25.2 | 8712 | 4.3 | 153 | 3.05 |
| comp H | 780 | 9 | 12 | 20 | 108 | 20 | 2160 | 3.4 | 114 | 3.23 |
| Ex 13 | 1176 | 19.1 | 16.2 | 25 | 309 | 25.2 | 7797 | 4.1 | 151 | 3.02 |
| Ex 14 | 195 | 12.25 | 25.2 | 45 | 309 | 25.2 | 7779 | 4.6 | 175 | 3.03 |
| Ex 15 | 390 | 12.25 | 20.1 | 40 | 246 | 25.2 | 6205 | 4.3 | 154 | 3.05 |
| Ex 16 | 390 | 12.25 | 25.2 | 45 | 309 | 25.2 | 7779 | 4.5 | 171 | 3.02 |
| Ex 17 | 390 | 12.25 | 14.6 | 40 | 179 | 16.2 | 2897 | 3.9 | 150 | 3.23 |
| Ex 18 | 390 | 12.25 | 33.5 | 50 | 410 | 27.6 | 11326 | 4.7 | 178 | 2.91 |
| Ex 19 | 390 | 12.25 | 23.2 | 45 | 284 | 27.6 | 7844 | 4.3 | 173 | 2.94 |
| Ex 20 | 390 | 12.25 | 22.6 | 45 | 277 | 26.8 | 7420 | 4.1 | 160 | 2.88 |
| comp I | 390 | 12.25 | 8.8 | 20 | 108 | 20 | 2156 | 3.5 | 118 | 3.07 |
| comp J | 390 | 12.25 | 2.2 | 10 | 27 | 28.1 | 757 | 2.8 | 96 | 2.74 |

TABLE 2

| | Creep test at 70° C./600 MPa | |
|---|---|---|
| | Creep rate ($s^{-1}$) | Creep life time (s) |
| Comp. Ex. H | $9.36 * 10^{-6}$ | $37.8 * 10^3$ |
| Ex. 16 | $2.93 * 10^{-6}$ | $80.0 * 10^3$ |
| Ex. 20 | $0.91 * 10^{-6}$ | $205.4 * 10^3$ |

TABLE 3

| | TMDSC non-reversible heat flow | | | TMDSC reversible heat flow | | | |
|---|---|---|---|---|---|---|---|
| | Peak 144° C. (J/g) | Peak 152° C. (J/g) | Total Enthalpy (J/g) | Peak <140° C. (J/g) | Peak 144° C. (J/g) | Peak 152° C. (J/g) | Total Enthalpy (J/g) |
| Spectra 900 | 190.8 | 0 | 190.8 | 16.6 | 52.5 | 6.4 | 72.6 |
| Spectra 1000 | 159.9 | 31.0 | 191.0 | 29.7 | 31.7 | 10.0 | 71.4 |
| Comp. F | 164.3 | 28.7 | 193.0 | 16.2 | 50.1 | 13.9 | 80.2 |
| Comp. H | 162.6 | 30.5 | 193.1 | 17.2 | 39.5 | 9.9 | 66.6 |
| Ex. 10 | 167.6 | 44.2 | 211.8 | 9.3 | 40.3 | 14.0 | 63.6 |
| Ex. 13 | 170.3 | 45.6 | 215.9 | 10.9 | 35.9 | 11.6 | 58.4 |
| Ex 19 | 155.2 | 46.9 | 202.1 | 9.8 | 49.2 | 16.8 | 75.8 |
| Ex. 20 | 152.1 | 52.3 | 204.4 | 10.4 | 44.7 | 19.3 | 74.5 |

TABLE 4

| | Preformed sheet | | Assembled sheets | | | |
|---|---|---|---|---|---|---|
| | | | number | | ballistic results | |
| | number of mono-layers | AD (g/m²) | of sheets | AD (kg/m²) | V50 (m/s) | SEA (J · m²/kg) |
| Ex. 21 | 4 | 103 | 20 | 2.0 | 407 | 322 |
| | | | 27 | 2.8 | 456 | 300 |

TABLE 4-continued

| | Preformed sheet | | Assembled sheets | | | |
|---|---|---|---|---|---|---|
| | | | number | | ballistic results | |
| | number of mono-layers | AD (g/m²) | of sheets | AD (kg/m²) | V50 (m/s) | SEA (J · m²/kg) |
| Ex. 22 | 4 | 94 | 33 | 3.4 | 487 | 280 |
| | | | 21 | 2.0 | 425 | 365 |
| | | | 30 | 2.8 | 466 | 307 |
| | | | 36 | 3.4 | 489 | 280 |
| Ex. 23 | 4 | 86 | 23 | 2.0 | 441 | 391 |
| | | | 33 | 2.8 | 482 | 324 |
| | | | 40 | 3.4 | 496 | 288 |
| Comp. K | 4 | 145 | 18 | 2.6 | 415 | 265 |
| | | | 24 | 3.4 | 468 | 258 |
| | | | 30 | 4.3 | 493 | 226 |
| Ex. 24 | 2 | 89 | 22 | 2.0 | 322 | 211 |
| | | | 31 | 2.6 | 435 | 272 |
| | | | 38 | 3.4 | 466 | 245 |
| Ex. 25 | 2 | 95 | 21 | 2.0 | 333 | 201 |
| | | | 29 | 2.6 | 426 | 263 |
| | | | 36 | 3.4 | 458 | 245 |
| Ex. 26 | 4 | 176 | 11 | 2.0 | 375 | 291 |
| | | | 16 | 2.6 | 455 | 296 |
| | | | 19 | 3.4 | 501 | 310 |
| Comp. L | 2 | 131 | 23 | 3.0 | 392 | 236 |
| | | | 26 | 3.5 | 417 | 205 |
| | | | 30 | 4.0 | 460 | 213 |

TABLE 5

| | Moulded panel | Ballistic performance | | |
|---|---|---|---|---|
| | Areal density (kg/m²) | Projectile | V50 (m/s) | SEA (J · m²/kg) |
| Ex. 27 | 2.0 | Parabellum | 485 | 479 |
| | 3.0 | Parabellum | 502 | 336 |
| | 3.0 | FSP | 583 | 62 |
| | 4.0 | FSP | 615 | 53 |
| | 16.0 | AK-47 | 843 | 180 |
| Ex. 28 | 2.0 | Parabellum | 469 | 442 |
| | 3.0 | Parabellum | 509 | 345 |
| | 3.0 | FSP | 502 | 44 |
| | 4.0 | FSP | 569 | 45 |
| | 16.0 | AK-47 | 809 | 165 |
| Comp. M | 2.6 | Parabellum | 395 | 240 |
| | 4.0 | FSP | 482 | 32 |
| | 19.0 | AK-47 | 810 | 140 |

The invention claimed is:

1. A ballistic-resistant assembly comprising a plurality of mono-layers consisting essentially of high-performance polyethylene multifilament yarn, the assembly having an areal density of at least 1.5 kg/m² and a specific energy absorption of at least 300 J·m²/kg as measured against a 9*19 mm FMJ Parabellum bullet according to a test procedure based on Stanag 2920.

2. The ballistic-resistant assembly according to claim 1, wherein the mono-layers contain uni-directionally oriented filaments, with the fibre direction in each mono-layer being rotated with respect to the fibre direction in an adjacent mono-layer.

3. The ballistic-resistant assembly according to claim 1, wherein the specific energy absorption of the panel is at least 325 J·m²/kg.

* * * * *